US008620439B2

(12) United States Patent
Lee et al.

(10) Patent No.: US 8,620,439 B2
(45) Date of Patent: Dec. 31, 2013

(54) APPARATUS CONTROLLING ELECTRICAL STIMULATION AND/OR HEALTH TRAINING/MONITORING

(75) Inventors: Jeong-hwan Lee, Gyeonggi-do (KR); Kun-soo Shin, Gyeonggi-do (KR); Wan-taek Han, Gyeonggi-do (KR); Hyung-sok Yeo, Gyeonggi-do (KR); Jin-sang Whang, Gyeonggi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 54 days.

(21) Appl. No.: 12/379,935

(22) Filed: Mar. 4, 2009

(65) Prior Publication Data

US 2009/0240305 A1 Sep. 24, 2009

Related U.S. Application Data

(62) Division of application No. 11/148,434, filed on Jun. 9, 2005, now abandoned.

(30) Foreign Application Priority Data

Jun. 10, 2004 (KR) .......................... 10-2004-0042507

(51) Int. Cl.
*A61N 1/18* (2006.01)
(52) U.S. Cl.
USPC ............................................................ 607/48
(58) Field of Classification Search
USPC .......... 600/382, 388, 390, 544; 607/2, 48-48, 607/65, 115
See application file for complete search history.

(56) References Cited

U.S. PATENT DOCUMENTS

| 5,070,873 | A | 12/1991 | Graupe et al. |
| 5,163,440 | A | 11/1992 | DeLuca et al. |
| 5,361,775 | A | 11/1994 | Remes et al. |
| 6,605,038 | B1 | 8/2003 | Teller et al. |
| 7,123,967 | B2 * | 10/2006 | Weinberg ........................ 607/48 |
| 2002/0010499 | A1 | 1/2002 | Rigaux et al. |
| 2002/0165590 | A1 * | 11/2002 | Crowe et al. .................... 607/48 |
| 2005/0209645 | A1 * | 9/2005 | Heruth et al. ..................... 607/3 |
| 2006/0235316 | A1 * | 10/2006 | Ungless et al. ............... 600/509 |

OTHER PUBLICATIONS

"A Study of Muscle Fatigue Index Searching in Terms of Median Frequency Analysis of EMG Signals During Isotonic Exercise", Hong et al. Journal of Biomedical Engineering Research; vol. 24, No. 3, 175-181; 2003.*

(Continued)

*Primary Examiner* — Carl H Layno
*Assistant Examiner* — Paula J Stice
(74) *Attorney, Agent, or Firm* — Staas & Halsey LLP

(57) ABSTRACT

An apparatus, method, and medium for generating electrical stimulation, including an electromyogram detector detecting an electromyographic signal of a body, a fatigue index calculator calculating a fatigue index indicating a degree of muscle fatigue by converting the electromyographic signal detected by the electromyogram detector during a predetermined time unit into a frequency-domain electromyographic signal, and an electrical stimulation signal generator adjusting an electrical stimulation signal according to the calculated fatigue index and generating the electrical stimulation signal. Accordingly, a health training/monitoring apparatus can include an electrical stimulation generator adjusting an electrical stimulation signal according to a degree of fatigue and generating the electrical stimulation signal, a physical activity monitor monitoring a physical activity using at least one of a heart rate measurer and an accelerometer, and a mode selector selectively driving the electrical stimulation generator or the physical activity monitor according to an amount of the physical activity.

6 Claims, 15 Drawing Sheets

(56) References Cited

OTHER PUBLICATIONS

U.S. Office Action for parent U.S. Appl. No. 11/148,434; mailed Nov. 26, 2007.

U.S. Office Action for parent U.S. Appl. No. 11/148,434; mailed Apr. 18, 2008.

U.S. Office Action for parent U.S. Appl. No. 11/148,434; mailed Sep. 26, 2008.

U.S. Advisory Action for parent U.S. Appl. No. 11/148,434; mailed Dec. 19, 2008.

* cited by examiner

Time / Div : 0.2s
Volt / Div : 0.5V

Time / Div : 0.2s
Volt / Div : 0.5V

APPARATUS CONTROLLING ELECTRICAL STIMULATION AND/OR HEALTH TRAINING/MONITORING

CROSS-REFERENCE TO RELATED APPLICATIONS

This application is a divisional application of U.S. patent application Ser. No. 11/148,434, filed Jun. 9, 2005 and now abandoned, the disclosure of which is herein incorporated in its entirety by reference. This application claims the priority benefit of Korean Patent Application No. 10-2004-0042507, filed on Jun. 10, 2004, the disclosures of which are herein incorporated in their entirety by reference.

BACKGROUND OF THE INVENTION

1. Field of the Invention

The present invention relates to a medical aid, and more particularly, to an apparatus, method, and medium controlling electrical stimulation using an electromyographic signal and/or health training/monitoring with the same.

2. Description of the Related Art

Conventional devices for electrically stimulating abdominal muscles to strengthen the abdominal muscles cannot quantitatively monitor the state of the abdominal muscles after abdominal muscle-strengthening exercise. Therefore, the conventional devices cannot display a corresponding electrical stimulation level, according to the state of abdominal muscles of each individual. Further, repeated abdominal muscle-strengthening exercise may aggravate fatigued abdominal muscles, with excessive exercise actually hindering the restoration of abdominal muscles and produce adverse effects.

In addition, since conventional heart monitors are worn around the chest, e.g., to measure heart rates, they can cause a sense of pressure upon the chest. In addition, conventionally, there have not been any apparatuses, methods, or media managing patients having difficulty with movement by monitoring their back muscles and walking patterns, in real time, nor have there been any apparatuses, methods, or media for measuring heart rates and stimulating abdominal muscles simultaneously.

SUMMARY OF THE INVENTION

Embodiments of the present invention provide apparatuses, methods, and media controlling electrical stimulation to a degree that the electrical stimulation does not aggravate fatigued muscles by calculating a degree of muscle fatigue by measuring a level of electromyogram (EMG) before and after muscle exercises.

Embodiments of the present invention also provides health training/monitoring apparatuses, methods, and media with such electrical stimulation, in which electrical stimulation may be controlled based on muscle fatigue, the degree of muscle fatigue can be monitored, information regarding physical activity and walking patterns can be monitored by measuring a heart rate and acceleration, while a user is performing aerobic exercises, such as running, jogging, walking, or stepping, and calories expended may be calculated.

To achieve the above and/or other aspects and advantages, embodiments of the present invention set forth an electrical stimulation apparatus using an electromyographic measurement, including an electromyogram detector detecting an electromyographic signal from a body, a fatigue index calculator calculating a fatigue index indicating a degree of muscle fatigue, for at least a muscle of the body, by converting the detected electromyographic signal, detected during a predetermined time unit, into a frequency-domain electromyographic signal, and an electrical stimulation signal generator adjusting an electrical stimulation signal, for application to the body, based on the calculated fatigue index and generating the electrical stimulation signal. Here, the electromyogram detector may include an electromyogram detection electrode.

The fatigue index calculator may include an initial median frequency output unit to measure an electromyogram at an initial point, of the predetermined time unit, to convert the measured initial point electromyogram into an initial frequency-domain electromyogram, and to output an initial median frequency, a final median frequency output unit to measure an electromyogram at a final point, of the predetermined time unit, to convert the measured final point electromyogram into a final frequency-domain electromyogram, and to output a final median frequency, and a fatigue index output unit to determine the fatigue index based on a ratio of a difference between the initial median frequency and the final median frequency to the initial median frequency.

The electrical stimulation signal generator may adjust the electrical stimulation signal by changing a size, a cycle, and/or a pattern of the electrical stimulation signal.

To achieve the above and/or other aspects and advantages, embodiments of the present invention set forth a method of generating electrical stimulation using an electromyographic signal, including detecting an electromyographic signal from a body using a predetermined medium for detecting an electromyogram, calculating a fatigue index indicating a degree of muscle fatigue, for a muscle of the body, by converting the detected electromyographic signal, detected during a predetermined time unit, into a frequency-domain electromyographic signal, and adjusting an electrical stimulation signal according to the calculated fatigue index and generating the adjusted electrical stimulation signal.

The calculating of the fatigue index may include measuring an initial electromyogram signal at an initial point, of the predetermined time unit, converting the measured initial point electromyogram signal into an initial frequency-domain electromyogram signal, and outputting an initial median frequency, measuring a final electromyogram signal at a final point, of the predetermined time unit, converting the measured final point electromyogram signal into a final frequency-domain electromyogram signal, and outputting a final median frequency, and determining the fatigue index based on a ratio of a difference between the initial median frequency and the final median frequency to the initial median frequency.

In the adjusting and generating of the electrical stimulation signal, the electrical stimulation signal may be adjusted by changing a size, a cycle, and/or a pattern of the electrical stimulation signal.

To achieve the above and/or other aspects and advantages, embodiments of the present invention set forth a health training/monitoring apparatus, including an electrical stimulation generator to adjust an electrical stimulation signal based on a degree of fatigue, of a muscle of a body, and generating the adjusted electrical stimulation signal, a physical activity monitor to monitor a physical activity of a user using at least one of a heart rate measurer and an accelerometer for the body, and a mode selector selectively driving the electrical stimulation generator or the physical activity monitor based on an amount of the monitored physical activity.

Here, the electrical stimulation generator may include an electromyogram detector to detect an electromyographic signal of the body, a fatigue index calculator to calculate a fatigue index indicating the degree of fatigue by converting the detected electromyographic signal, detected during a predetermined time unit, into a frequency-domain electromyographic signal, and an electrical stimulation signal generator to adjust the electrical stimulation signal based on the calculated fatigue index and to generate the adjusted electrical stimulation signal.

The physical activity monitor may include the heart rate measurer to measure a heart rate using a predetermined electrode attached to the body, the accelerometer to measure an acceleration of physical movement of the body; and an activity output unit to output at least one of a physical activity pattern and calories expended based on the measured heart rate and/or the measured acceleration. In addition, the accelerometer may measure the acceleration of the physical movement in any one of a one-axis direction, two-axis direction, or three-axis direction.

Further, the mode selector may drive the physical activity monitor when an output waveform of the accelerometer is greater than a predetermined threshold value and drives the electrical stimulation generator when the output waveform of the accelerometer is not greater than the predetermined threshold value.

The apparatus may also be a waist belt or a patch. The waist belt or the patch may include a first layer including a plurality of electrodes for measuring the heart rate, a plurality of electrodes for the electrical stimulation, and a plurality of electrodes for the measuring of the electromyographic signal, and a second layer including the accelerometer measuring the acceleration of the physical movement and a predetermined controller. An airbag layer inflatable and deflatable by air may also be interposed between the first layer and the second layer.

To achieve the above and/or other aspects and advantages, embodiments of the present invention set forth a health training/monitoring method, including determining whether a physical activity is dynamic or static, monitoring the physical activity using at least one of a heart rate measurer and an accelerometer when the physical activity is dynamic, and adjusting an electrical stimulation signal based on a degree of muscle fatigue, of at least a muscle of a body, and generating the adjusted electrical stimulation signal when the physical activity is static.

In the determining of whether the physical activity is dynamic or static, the physical activity may be determined to be dynamic when a value of the physical activity is greater than a predetermined threshold value for a predetermined period of time, and the physical activity may be determined as static when a value of the physical activity is not greater than the predetermined threshold value for the predetermined period of time.

Further, the monitoring of the physical activity may include measuring the heart rate using a predetermined electrode attached to the body when the physical activity is dynamic, measuring acceleration of physical movement of the body using an accelerometer, and outputting at least one of a physical activity pattern and calories expended using the measured heart rate and the measured acceleration. In addition, the adjusting and generating of the electrical stimulation signal may include detecting an electromyographic signal of the body, calculating a fatigue index indicating the degree of muscle fatigue by converting the detected electromyographic signal, detected during a predetermined time unit, into a frequency-domain electromyographic signal, and adjusting the electrical stimulation signal based on the calculated fatigue index and generating the adjusted electrical stimulation signal.

To achieve the above and/or other aspects and advantages, embodiments of the present invention set forth an electrical stimulation apparatus, including an electromyogram detector detecting electromyographic signals from a body, a fatigue index calculator calculating a fatigue index indicating a degree of muscle fatigue, for at least a muscle in a body, by converting at least two detected electromyographic signals into respective frequency-domain electromyographic signals, with the calculated fatigue index being based on a ratio with the at least two frequency-domain electromyographic signals, and an electrical stimulation signal generator generating an electrical stimulation signal, for application to the body, based on the calculated fatigue index.

The apparatus may further include a heart rate measurer to measure a heart rate using a predetermined electrode attached to the body, and an activity output unit to output at least one of a physical activity pattern and calories expended based on the measured heart rate. Further, the apparatus may include an accelerometer to measure an acceleration of physical movement of the body, and an activity output unit to output at least one of a physical activity pattern and calories expended based on the measured acceleration. Here, when the measured acceleration is greater than a predetermined threshold value the electrical stimulation signal generator may not generate the electrical stimulation signal.

The at least two detected electromyographic signals may be detected at least at an initial point in a predetermined period and a final point in the predetermined period, respectively. The initial point may occur when the electrical stimulation apparatus is applied to operate on the body, and the final point may occur when the electrical stimulation apparatus is removed from operating on the body.

To achieve the above and/or other aspects and advantages, embodiments of the present invention set forth media including computer readable code implementing embodiments of the present invention.

Additional aspects and/or advantages of the invention will be set forth in part in the description which follows and, in part, will be apparent from the description, or may be learned by practice of the invention.

BRIEF DESCRIPTION OF THE DRAWINGS

The above and/or other features and advantages of the present invention will become more apparent by describing in detail exemplary embodiments thereof with reference to the attached drawings in which.

DETAILED DESCRIPTION OF THE PREFERRED EMBODIMENTS

Figure 1:
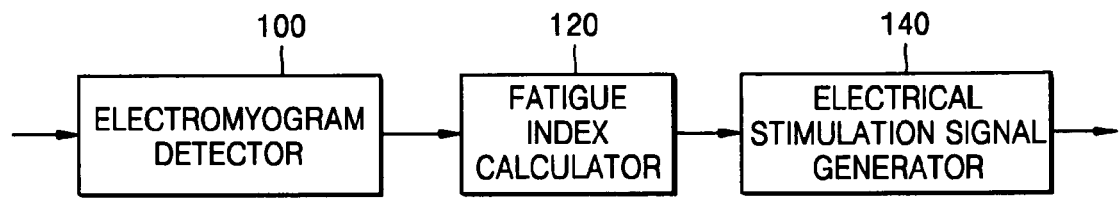
FIG. 1 illustrates a block diagram of an apparatus controlling electrical stimulation using an electromyographic signal, according to an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

FIG. 1 illustrates a block diagram of an apparatus for controlling electrical stimulation using an electromyographic signal, according to an embodiment of the present invention. The apparatus can include an electromyogram (EMG) detector 100, a fatigue index calculator 120, and an electrical stimulation signal generator 140.

The EMG detector 100 detects an electromyographic signal of the body, and can be detected using an EMG detection electrode, for example. The EMG detection electrode is attached to the abdomen to monitor a degree of abdominal muscle fatigue, before and after exercise. In addition, the EMG detection electrode can be attached to the back, along the waist, to monitor a degree of back muscle fatigue for those with back pain, for example.

Figure 2:
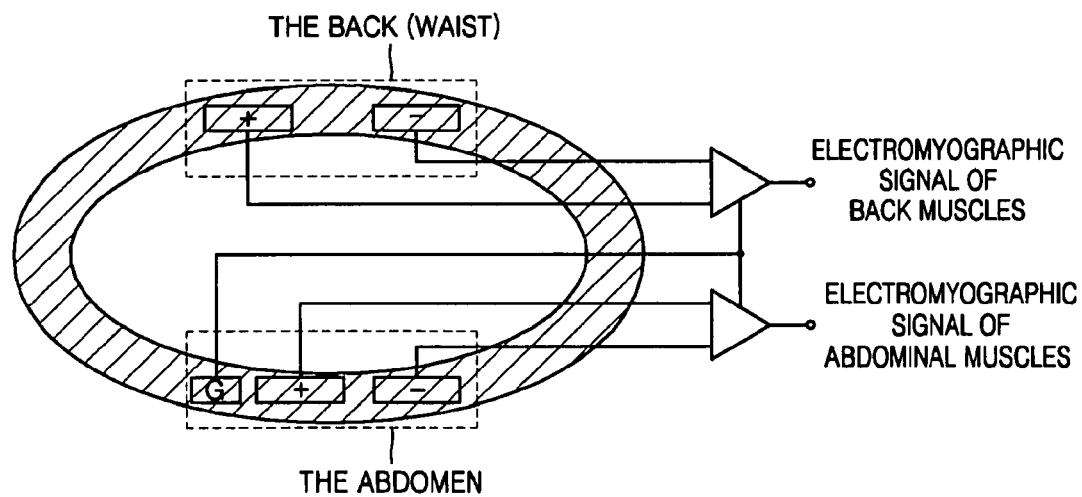
FIG. 2 illustrates a belt including an electromyogram (EMG) detection electrode to monitor a degree of abdominal/back muscle fatigue based on a biological signal, and an amplifier amplifying a detected signal, according to an embodiment of the present invention.

FIG. 2 illustrates a belt including an EMG detection electrode to monitor the degree of abdominal/back muscle fatigue, based on a biological signal, and an amplifier amplifying a detected signal.

The fatigue index calculator 120 can calculate a fatigue index indicating the degree of muscle fatigue by converting an electromyographic signal detected by the EMG detector 100, during a predetermined time unit, into a frequency-domain signal.

Figure 3:
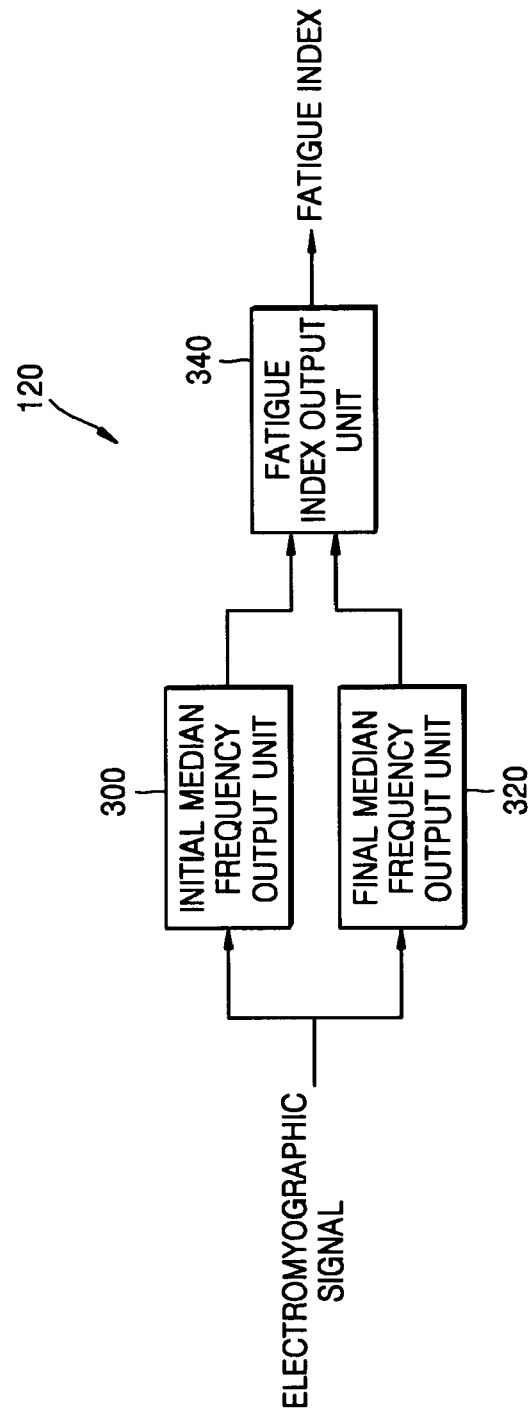
FIG. 3 illustrates a detailed block diagram of a fatigue index calculator, e.g., such as that illustrated in FIG. 1.

FIG. 3 illustrates a detailed block diagram of a fatigue index calculator 120, with the fatigue index calculator 120 including an initial median frequency output unit 300, a final median frequency output unit 320, and a fatigue index output unit 340. The initial median frequency output unit 300 measures an EMG at an initial point, of a predetermined time unit, converts the EMG into a frequency-domain EMG, and outputs a median frequency (initial median frequency). The final median frequency output unit 320 measures an EMG at a final point of the predetermined time unit, converts the EMG into a frequency-domain EMG, and outputs another median frequency (final median frequency). The fatigue index output unit 340 determines a fatigue index as a ratio of a difference between the initial median frequency and the final median frequency to the initial median frequency.

The electrical stimulation signal generator 140 can generate an electrical stimulation signal according to the fatigue index. The electrical stimulation signal generator 140 can adjust a size, a cycle, and/or a pattern of an electrical stimulation signal, for example.

Figure 4:
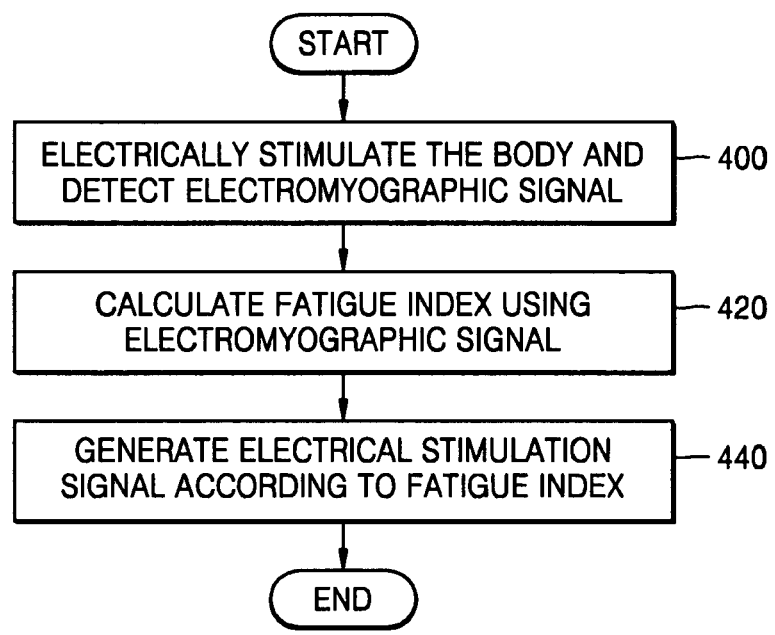
FIG. 4 illustrates a flowchart for a method for generating an electrical stimulation signal, according to an embodiment of the present invention.

FIG. 4 illustrates a flowchart for generating an electrical stimulation signal, according to an embodiment of the present invention.

An electromyographic signal of the body can be detected using an electromyographic signal detection electrode attached to a predetermined EMG detection medium, such as the belt illustrated in FIG. 2 (operation 400). The electromyographic signal detected, during a predetermined time unit, can be converted into a frequency-domain electromyographic signal and a fatigue index, indicating the degree of muscle fatigue, can be calculated using the frequency-domain electromyographic signal (operation 420).

Here, the predetermined time unit can be a time unit for measuring a median frequency and may be set arbitrarily. For example, the moment when the belt to which the EMG detection electrode is attached is worn may be set as a starting point and the moment when the belt is taken off may be set as a final point. Alternatively, a period between the starting and the final points may be divided into several sections, and starting and final points of each section may be set as the time unit for measuring the median frequency.

Figure 5:
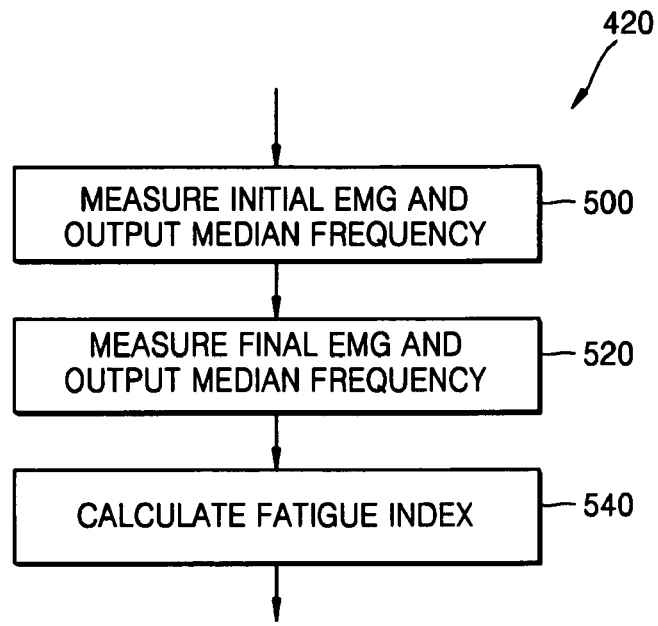
FIG. 5 illustrates a flowchart for a method for calculating a fatigue index, e.g., such as in operation 420 of FIG. 4.

FIG. 5 illustrates a flowchart for calculating the fatigue index in operation 420, for example, in greater detail. Referring to FIG. 5, after the belt is worn, an EMG signal at the initial point of the predetermined time unit for measuring the median frequency may be measured and the EMG signal is converted into a frequency-domain signal. As a result, an initial median frequency $f_{mi}$ can then be output (operation 500).

After carrying out daily activities or exercising, the EMG signal at the final point of the predetermined time can be measured and the EMG signal converted into a frequency-domain signal. As a result, a final median frequency $f_{mf}$ can be output (operation 520).

Once the initial median frequency $f_{mi}$ and the final median frequency $f_{mf}$ are obtained, the fatigue index may be calculated as a ratio of a difference between the initial median frequency $f_{mi}$ and the final median frequency $f_{mf}$ (operation 540) to the initial median frequency $f_{mi}$. If the fatigue index is obtained using an EMG electrode attached to abdominal muscles the degree of abdominal fatigue can be monitored. If the fatigue index is obtained using an EMG electrode attached to back muscles the degree of back muscle fatigue can be monitored.

$$\text{Fatigue Index}(\%) = \frac{f_{mi} - f_{mf}}{f_{mi}} \times 100. \quad \text{Equation (1)}$$

Once the fatigue index is calculated, in operation 420, an electrical stimulation signal corresponding to the fatigue index can be generated so as to not increase muscle fatigue (operation 440). The electrical stimulation signal can be adjusted by changing its size, cycle, and/or pattern, for example.

A health training/monitoring apparatus, method, and medium, according to an embodiment of the present invention will now be described.

Figure 6:
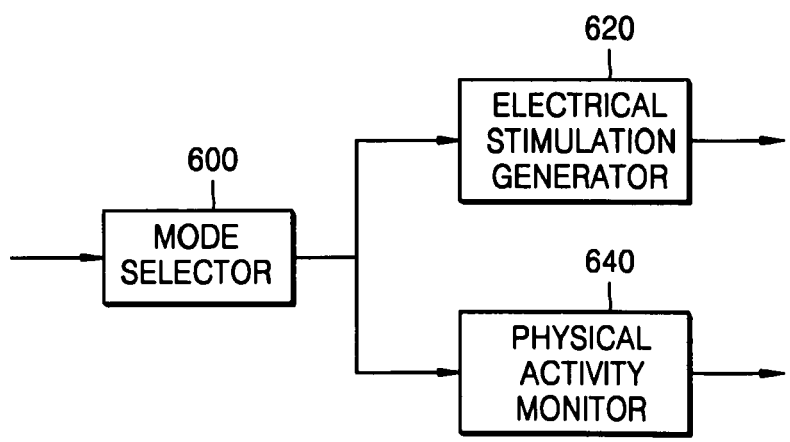
FIG. 6 illustrates a block diagram of a health training/monitoring apparatus, according to an embodiment of the present invention.

FIG. 6 illustrates a block diagram of the health training/monitoring apparatus, according to an embodiment of the present invention. The health training/monitoring apparatus can include an electrical stimulation generator 620, a physical activity monitor 640, and a mode selector 600.

The electrical stimulation generator 620 generates an electrical stimulation signal, adjusted according to the degree of muscle fatigue. A detailed description of the electrical stimulation generator 620 will be omitted here since it can be similar to the aforementioned apparatus generating electrical stimulation of FIG. 1.

Figure 7:
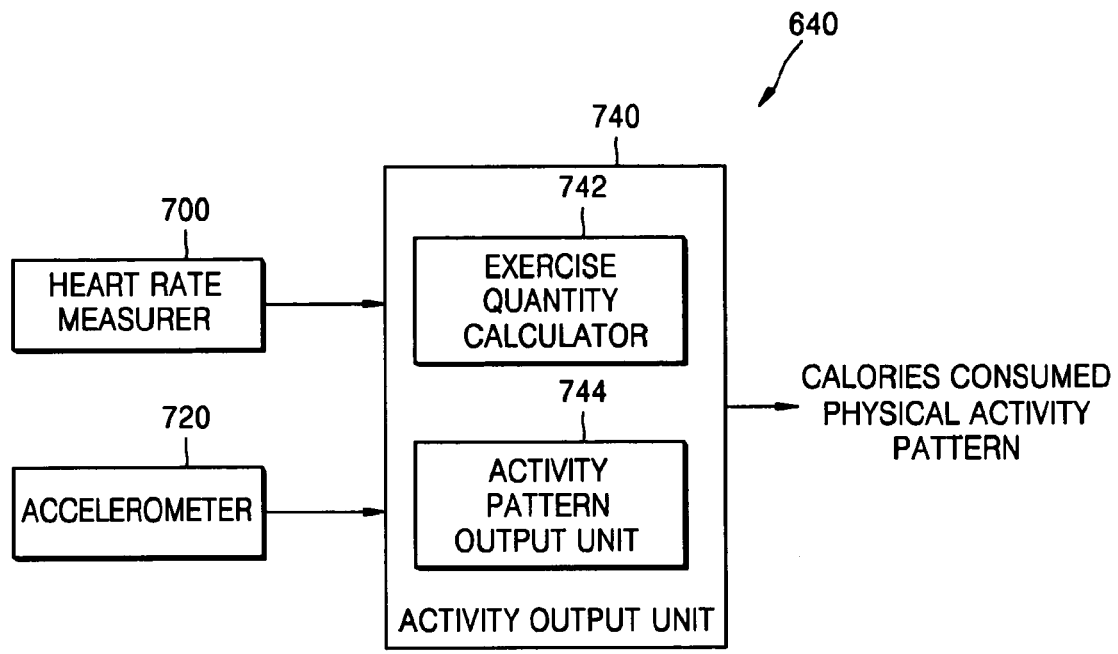
FIG. 7 illustrates a detailed block diagram of a physical activity monitor, such as that illustrated in FIG. 6, according to an embodiment of the present invention.

The physical activity monitor 640 can monitor physical activity, using at least one of a heart rate measurer and an accelerometer. FIG. 7 is a detailed block diagram of the physical activity monitor 640. As illustrated, the physical activity monitor 640 can include a heart rate measurer 700, an accelerometer 720, and an activity output unit 740.

The heart rate measurer 700 measures a heart rate using a predetermined electrode attached to the body, for example. The accelerometer 720 measures acceleration of physical movement. The accelerometer 720 can measure the acceleration of physical movement in any one of one-axis direction, two-axis direction, or three-axis direction, for example. The one-axis direction denotes one direction in which the body moves, such as the direction in front of the body. The two-axis direction denotes two directions in which the body moves, such as front and right & left, for example. The three-axis direction denotes three directions such as front & rear, right & left, and top & bottom, for example.

The activity output unit 740 can output at least one of a physical activity pattern and calories expended (i.e., consumed by an activity) using the heart rate measured by the heart rate measurer 700 and the acceleration measured by the accelerometer 720. The activity output unit 740 includes an exercise quantity calculator 742 and an activity pattern output unit 744. The exercise quantity calculator 742 can calculate an amount of exercise using a heart rate and acceleration, with the activity pattern output unit 744 determining the corresponding activity pattern, such as walking, running, or ascending/descending stairs, using the heart rate and acceleration.

If an acceleration sensor (acceleration electrode) is attached to each of the front and rear of a belt worn around the waist, the walking pattern of a user can be monitored using the acceleration detected by the acceleration sensor (acceleration electrode). If an EMG sensor (EMG electrode) is also placed around the waist, along the back, the degree of back muscle fatigue can be monitored using an electromyographic signal detected by the EMG sensor (EMG electrode). In this regard, activity information of patients having difficulty with movement can be monitored all the time using their walking patterns and the varying degrees of muscle fatigue, thereby producing information useful for rehabilitative training, for example.

The mode selector 600, illustrated in FIG. 6, selectively drives the electrical stimulation generator 620 and the activity output unit 740 of the physical activity monitor 640 depending on the degree of physical activity. The degree of the physical activity may be determined by the mode selector 600 based on an output waveform of the accelerometer 720 being greater than a predetermined threshold for a predetermined period of time. For example, when a value of the output waveform of the accelerometer 720 is greater than a predetermined threshold value for a predetermined period of time, the mode of the physical activity can be designated a dynamic mode. Conversely, when the value of the output waveform of the accelerometer 720 is not greater than the predetermined threshold value for the predetermined period of time, the mode of the physical activity can be designated a static mode. The mode may also be selected manually by a user, for example.

Figure 8:
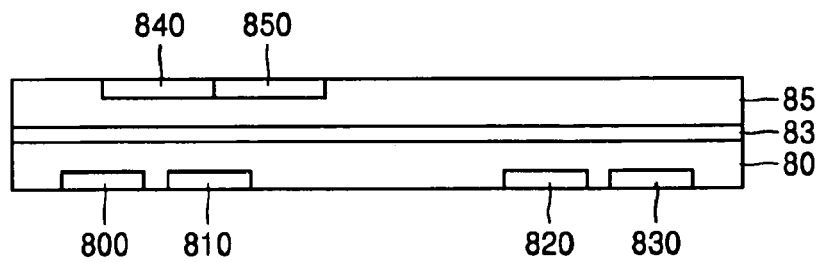
FIG. 8 is a sectional view of a waist belt or a patch, according to an embodiment of the present invention.

A health training/monitoring apparatus using electrical stimulation may take the form of a belt worn around the waist or a patch worn around the arm, for example. FIG. 8 is a sectional view of such a waist belt or patch. The waist belt or the patch can include a first layer 80 and a second layer 85, for example. The first layer 80 may include a plurality of electrodes 800 and 810 for measuring a heart rate, a plurality of electrodes 820 and 830 for electrical stimulation, and a plurality of electrodes 800 and 810 for measuring electromyographic signals. The second layer 85 can include an accelerometer 840 measuring acceleration and a predetermined controller 850.

In addition, the belt or patch may include an airbag layer 83, inflatable or deflatable by air, which may be interposed between the first layer 80 and the second layer 85. When the belt or the patch is worn around the waist or the arm, the airbag layer 83 can keep the belt or the patch close to the waist or the arm to prevent it from moving to the right/left or sliding up/down during physical activities, e.g., such during exercising.

Figure 9:
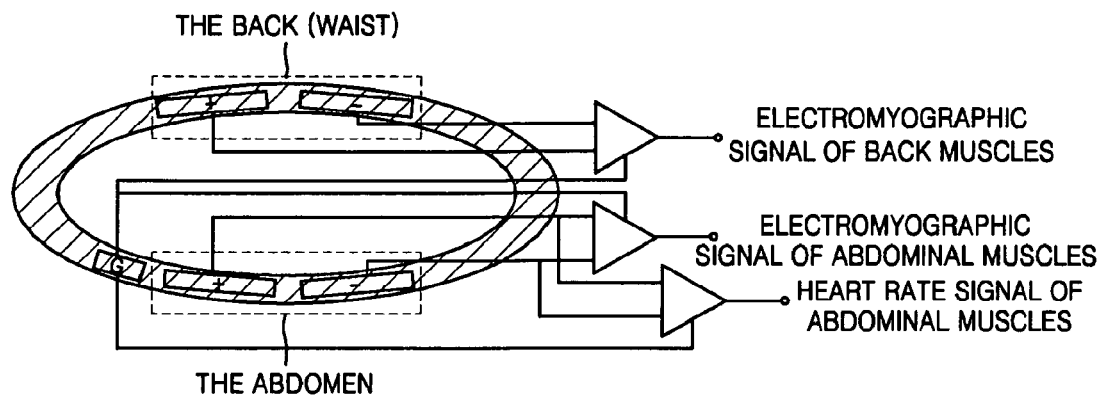
FIG. 9 illustrates a belt including an EMG detection electrode and an electrode for detecting a heart rate of abdominal muscles and to monitor a degree of abdominal/back fatigue using a biological signal, and an amplifier amplifying the detected signal, according to an embodiment of the present invention.
Figure 10:
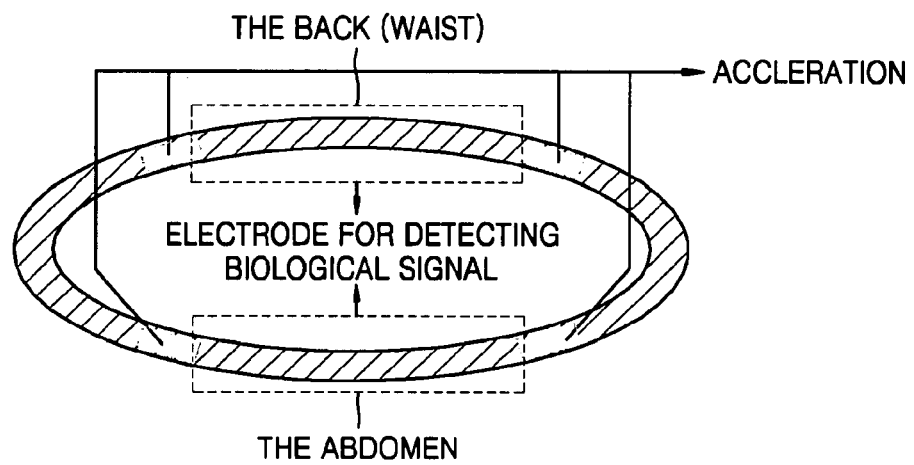
FIG. 10 illustrates a belt including a biological signal detection electrode to monitor an activity using an acceleration signal, according to an embodiment of the present invention.
Figure 11A:
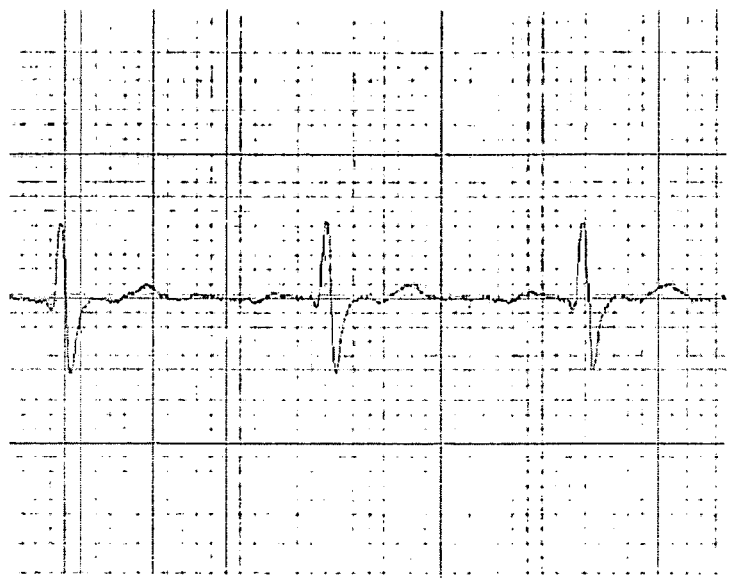
FIG. 11A illustrates an abdomen EMG when electrodes are attached to the upper and lower abdomen, according to an embodiment of the present invention.
Figure 11B:
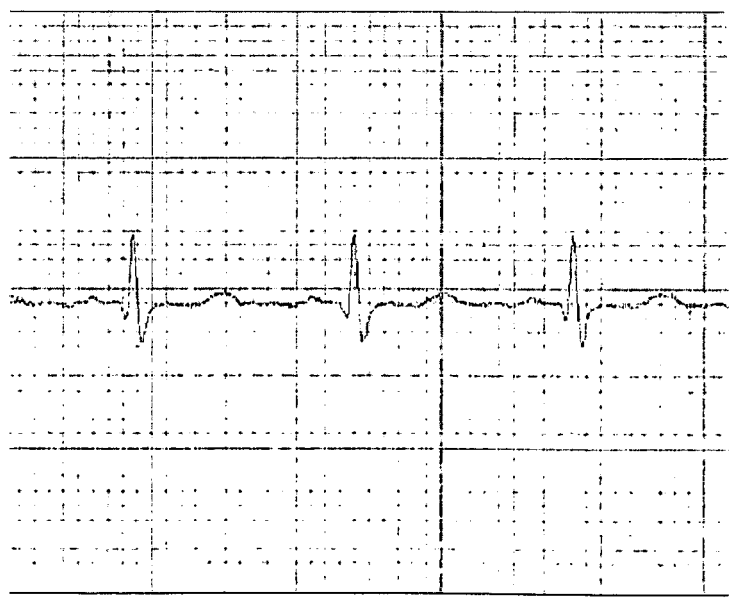
FIG. 11B illustrates an abdomen EMG when electrodes are attached to the right and left sides of the abdomen, according to an embodiment of the present invention.

FIG. 9 illustrates a belt including an EMG detection electrode, and an electrode for detecting a heart rate, for abdominal muscles to monitor the degree of abdominal/back fatigue using a biological signal, and an amplifier amplifying a corresponding detected signal. FIG. 10 illustrates a belt including a biological signal detection electrode for monitoring activity using an acceleration signal. FIG. 11A illustrates an abdomen EMG when electrodes are attached to the upper and lower abdomen, according to an embodiment of the present invention, and FIG. 11B illustrates an abdomen EMG when electrodes are attached to the right and left sides of the abdomen, according to an embodiment of the present invention.

Figure 12:
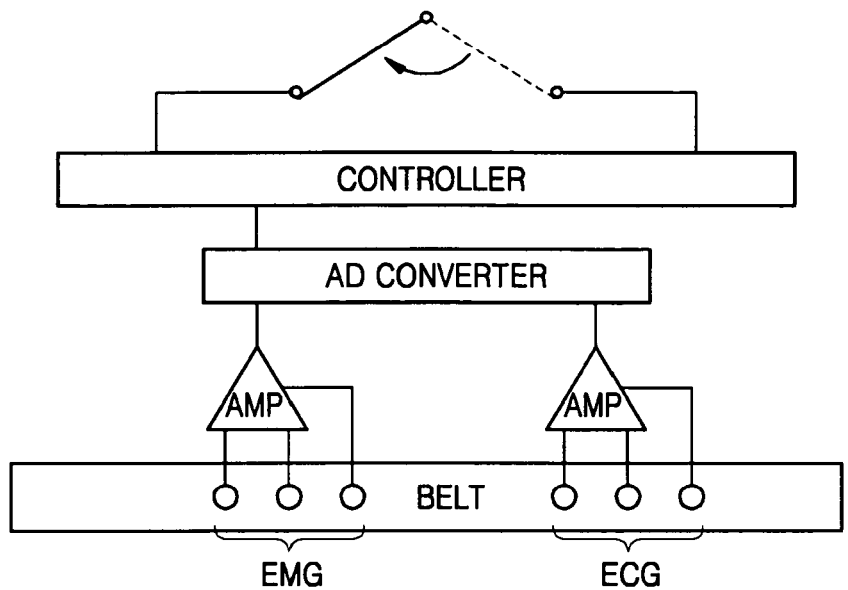
FIG. 12 illustrates a schematic configuration of the health training/monitoring apparatus detecting a signal for monitoring the degree of abdominal/back fatigue and a heart rate using a biological signal, when a physical activity is in a static mode, according to an embodiment of the present invention.
Figure 13:
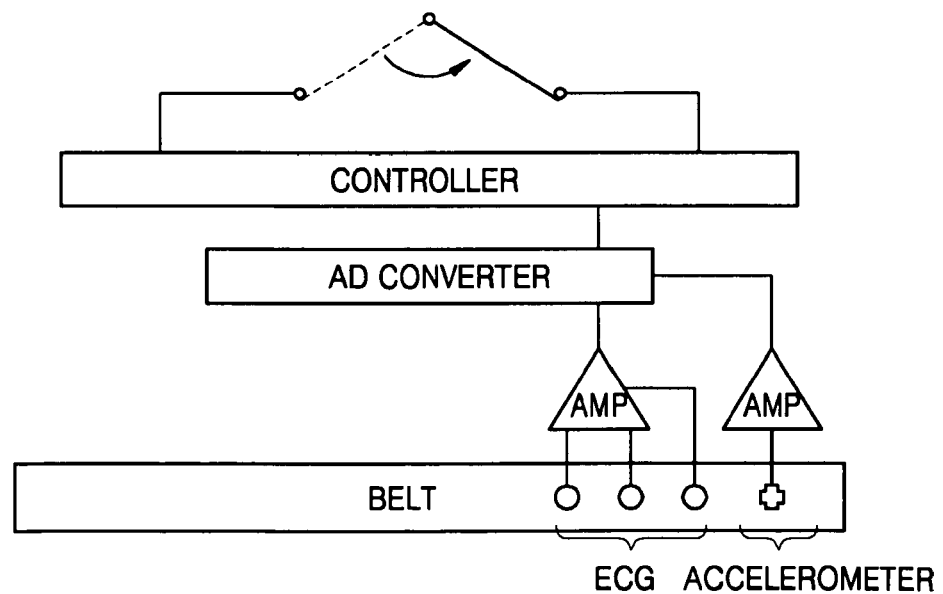
FIG. 13 illustrates a schematic configuration of the health training/monitoring apparatus detecting a signal for monitoring a physical activity, using an acceleration signal, to estimate calories expended and monitor a walking pattern, when the physical activity is in a dynamic mode, according to an embodiment of the present invention.

FIG. 12 illustrates a schematic configuration of a health training/monitoring apparatus detecting a signal monitoring a degree of abdominal/back fatigue, and a heart rate, using a biological signal when a physical activity is in the aforementioned static mode, according to an embodiment of the present invention. FIG. 13 illustrates a schematic configuration of a health training/monitoring apparatus detecting a signal monitoring physical activity using an acceleration signal to estimate calories expended and to monitor a walking pattern when the physical activity is in the aforementioned dynamic mode, according to an embodiment of the present invention.

Figure 14:
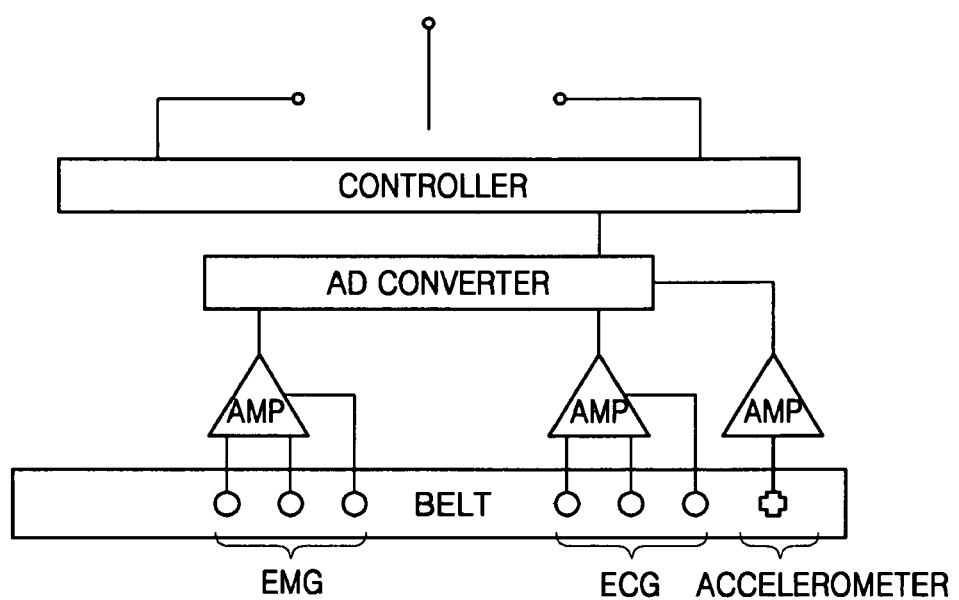
FIG. 14 illustrates a schematic configuration of a health training/monitoring apparatus detecting a signal for monitoring a degree of abdominal fatigue, a heart rate, and a walking pattern by monitoring an EMG, the heart rate, and an activity of a patient having difficulty with movement or a patient with back pain, according to an embodiment of the present invention.
Figure 15:
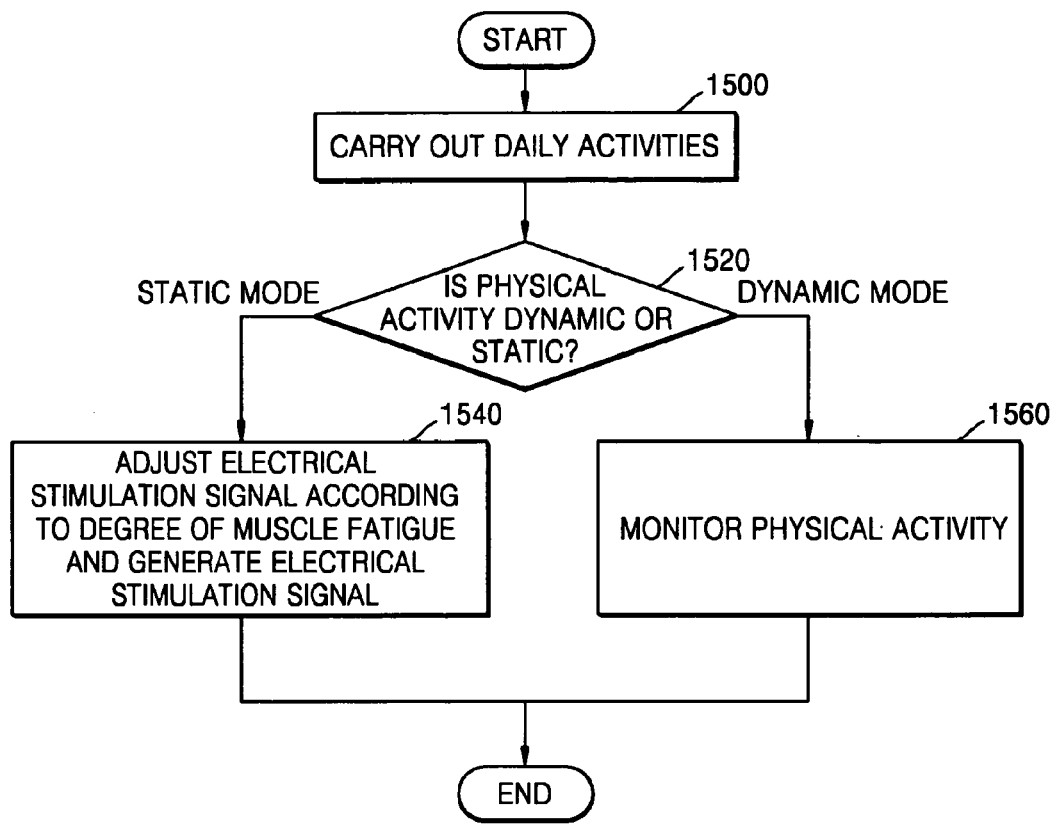
FIG. 15 illustrates a flowchart illustrating a method of generating an electrical stimulation signal, according to an embodiment of the present invention.

FIG. 14 illustrates a schematic configuration of a health training/monitoring apparatus monitoring a degree of abdominal fatigue, a heart rate, and a walking pattern by monitoring an EMG, the heart rate, and an activity of a patient having difficulty with movement or a patient with back pain, according to an embodiment of the present invention. FIG. 15 illustrates a flowchart for generating an electrical stimulation signal, according to an embodiment of the present invention. The operation of the health training/monitoring apparatus will now be described with reference to FIG. 15.

During daily activities (operation 1500), when a belt or a patch is worn around the body, the mode selector 600 determines whether a physical activity is in a dynamic or static mode (operation 1520). When the physical activity is greater than a predetermined threshold value, for a predetermined period of time, the mode selector 600 designates the mode of the physical activity as being dynamic. Otherwise, the mode selector 600 designates the mode of the physical activity as being static.

When the physical activity is in the static mode, the electrical stimulation generator 620 can adjust and generate an electrical stimulation signal according to a detected degree of muscle fatigue (operation 1540). The degree of fatigue can be determined by a fatigue index, e.g., as calculated by the above Equation 1, with a method of adjusting the electrical stimulation signal being similar to the above mentioned method of generating an electrical stimulation signal, discussed with relation to FIG. 4.

When the physical activity is in the dynamic mode, the physical activity monitor 640 can monitor the physical activity using at least one of the heart rate measurer 700 and the accelerometer 720 (operation 1560), for example.

Figure 16:
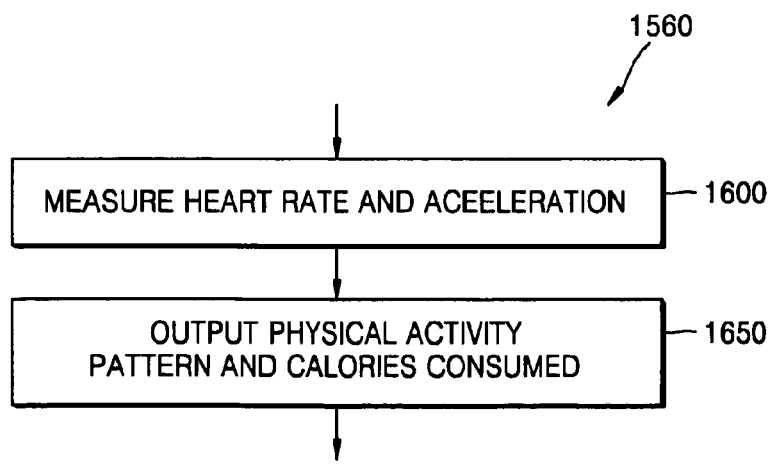
FIG. 16 illustrates a flowchart for monitoring a physical activity, such as operation 1560 of FIG. 15, according to an embodiment of the present invention.

FIG. 16 illustrates a flowchart for monitoring the physical activity, of operation 1560, in greater detail. When the physical activity is designated as corresponding to the dynamic mode, the heart rate can be measured using a predetermined electrode attached to the body, and acceleration of physical movement can be measured using the accelerometer 720 (operation 1600). At least one of a physical activity pattern and calories expended can be determined based on information regarding the measured heart rate and acceleration (operation 1650).

Figure 17:
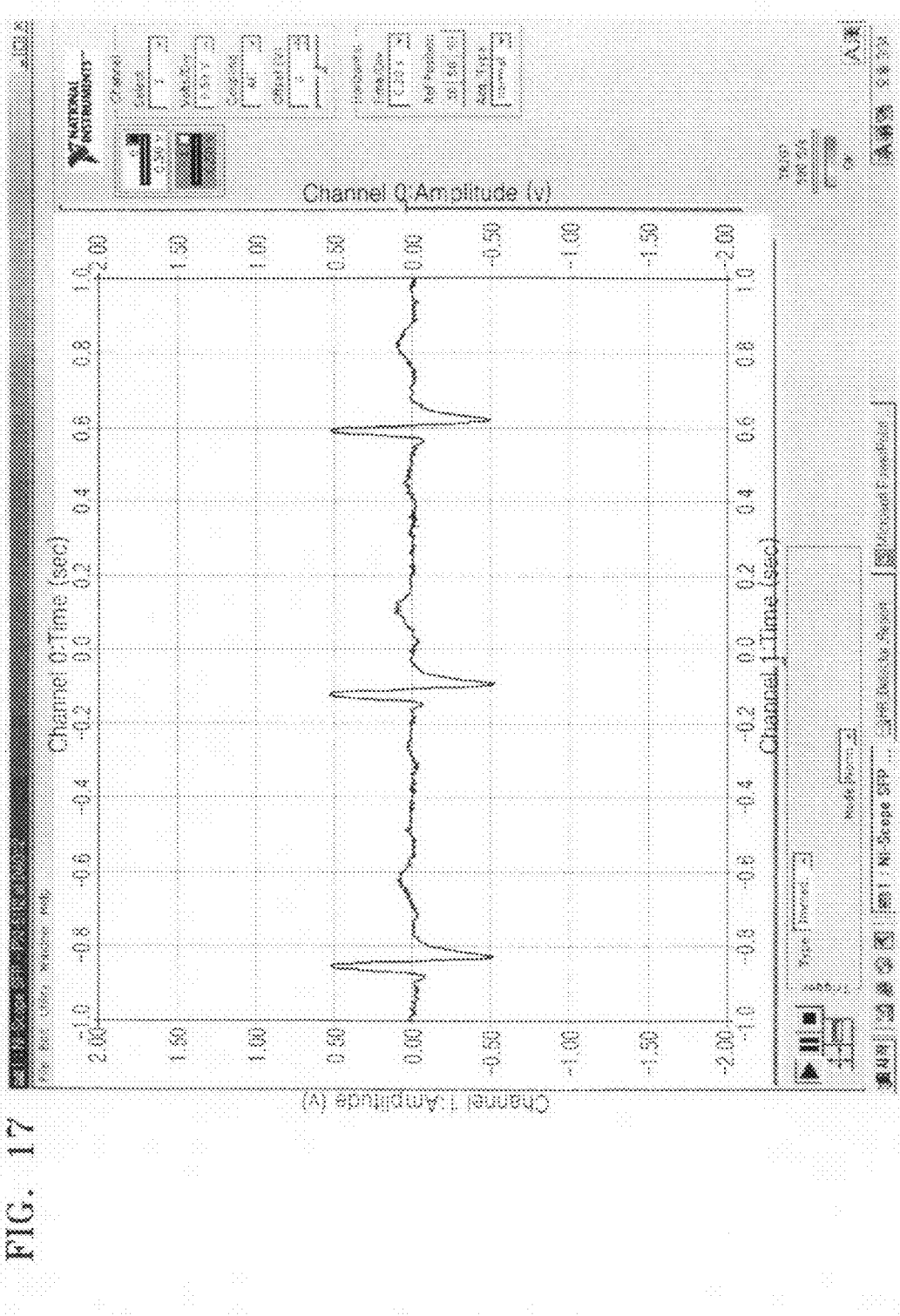
FIG. 17 illustrates a waveform diagram of a heart rate measured by electrodes attached to the upper and lower abdomen when a belt is worn around the waist, according to an embodiment of the present invention.
Figure 18:
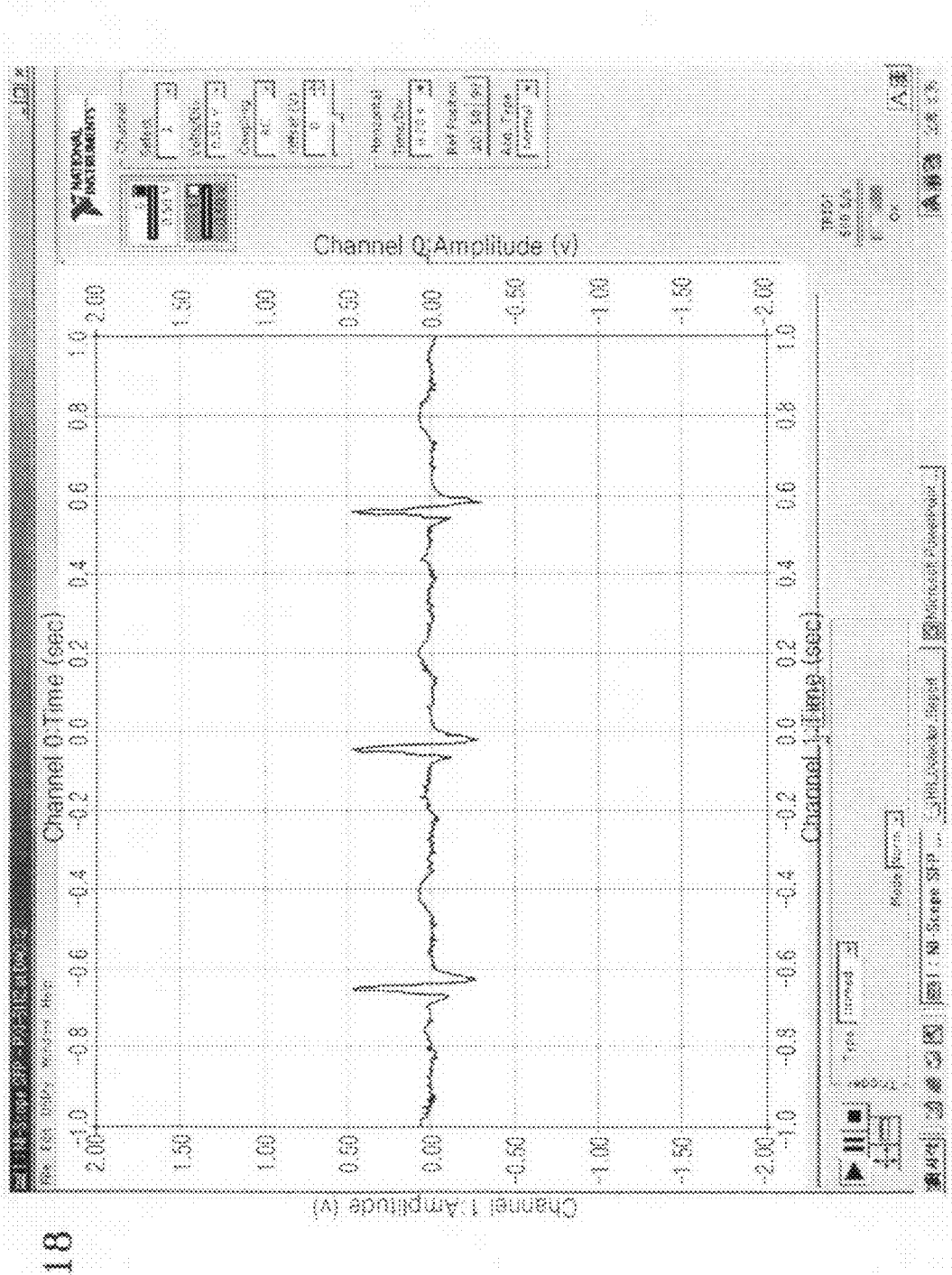
FIG. 18 illustrates a waveform diagram of a heart rate measured by electrodes attached to the right and left sides of the abdomen when the belt is worn around the waist, according to an embodiment of the present invention.

FIGS. 17 through 21 illustrate waveform diagrams of a heart rate measured by electrodes attached to the abdomen, according to an embodiment of the present invention. FIG. 17 illustrates a waveform diagram of a heart rate measured by electrodes attached to the upper and lower abdomen when a belt is worn around the waist. FIG. 18 illustrates a waveform diagram of a heart rate measured by electrodes attached to the right and left sides of the abdomen or the right and left parts of the right or left side of the abdomen when the belt is worn around the waist.

Figure 19:
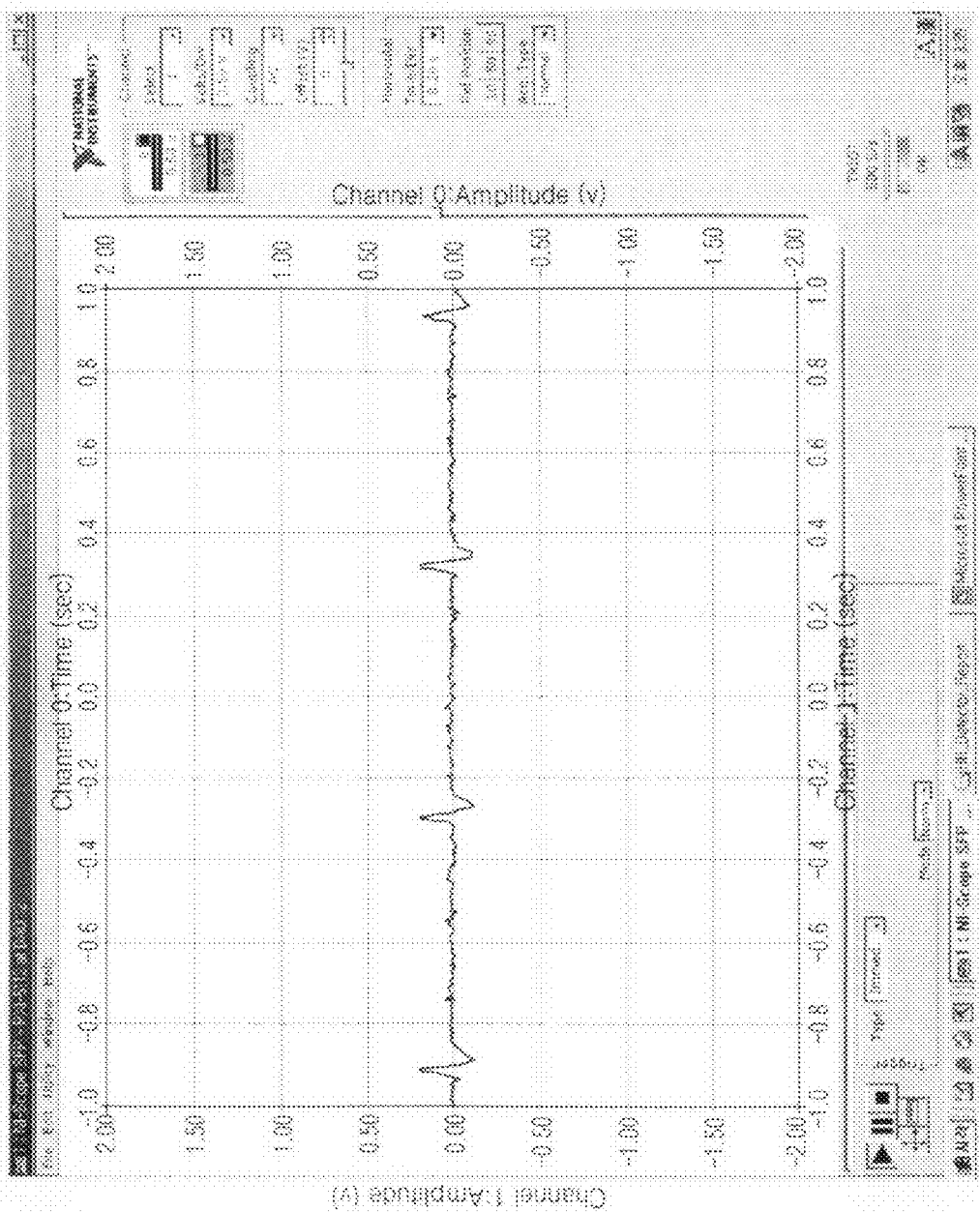
FIG. 19 illustrates a waveform diagram of a heart rate measured by electrodes attached to the right and left parts of the left side of the abdomen when the belt is worn around the waist, according to an embodiment of the present invention.
Figure 20:
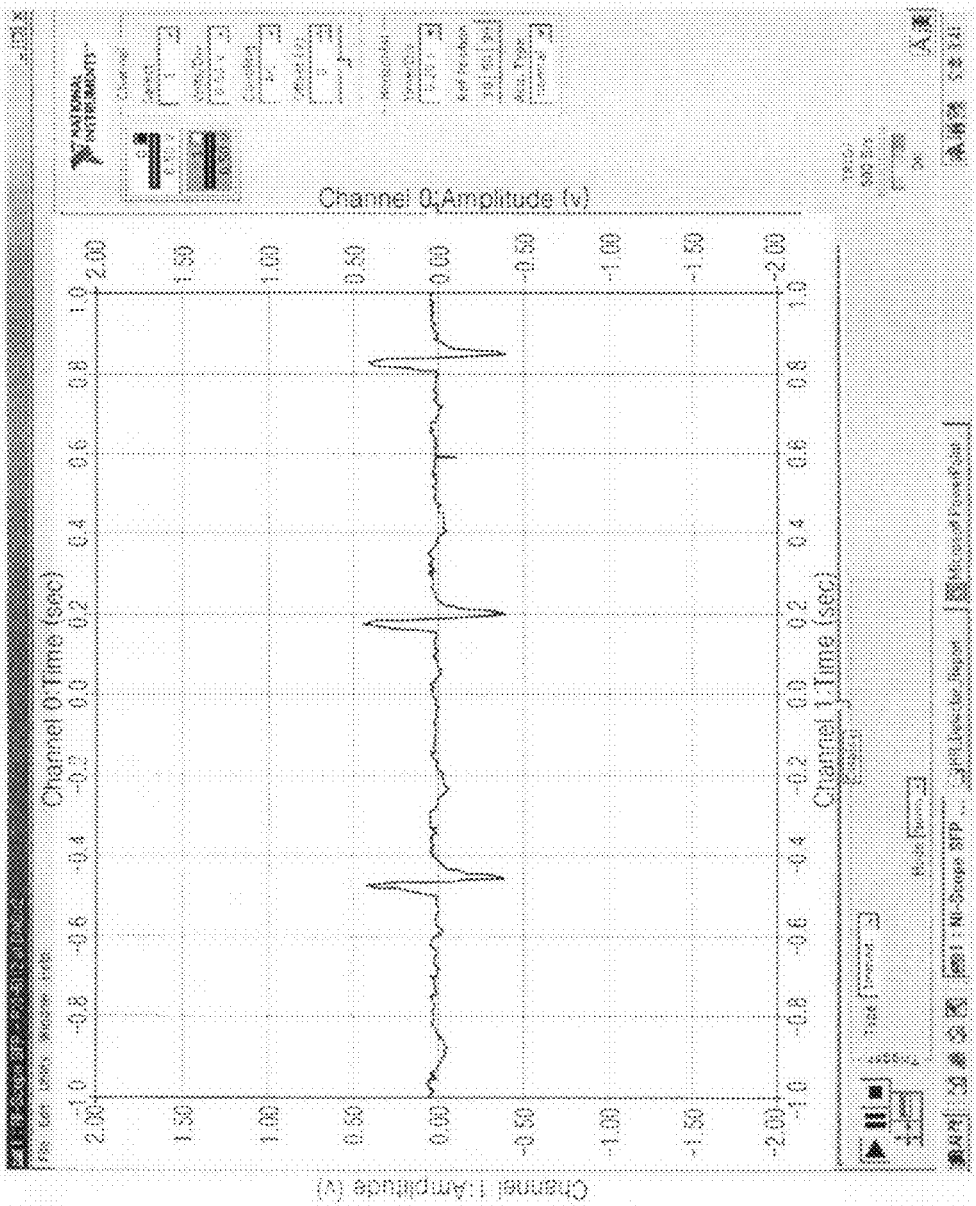
FIG. 20 illustrates a waveform diagram of a heart rate measured by electrodes attached to the right and left sides of the abdomen when the belt is worn around the waist, according to an embodiment of the present invention.
Figure 21:
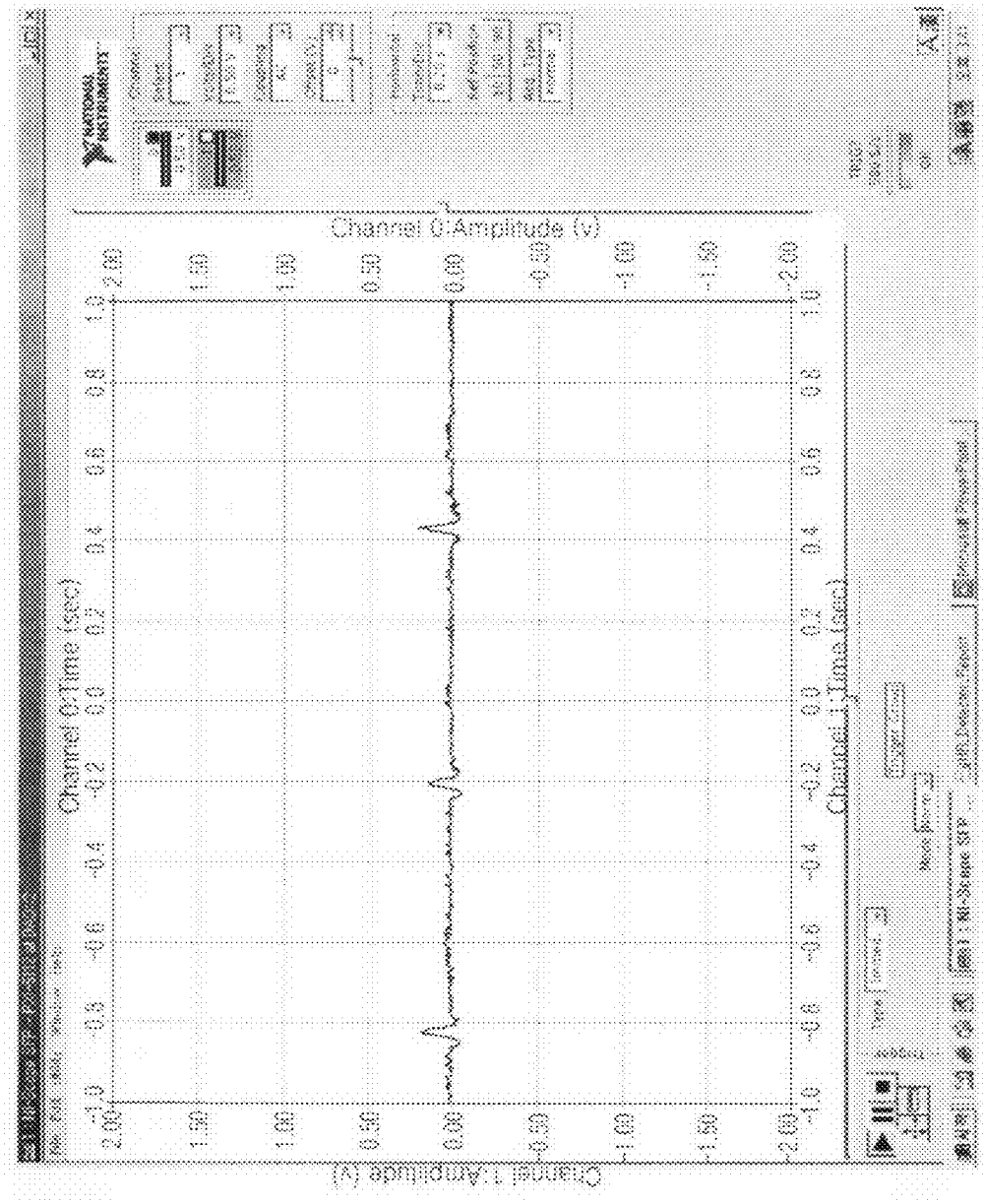
FIG. 21 illustrates a waveform diagram of a heart rate measured by electrodes attached to the right and left parts of the right side of the abdomen when the belt is worn around the waist, according to an embodiment of the present invention.

FIG. 19 illustrates a waveform diagram of a heart rate measured by electrodes attached to the right and left parts of the left side of the abdomen when the belt is worn around the waist, FIG. 20 illustrates a waveform diagram of a heart rate measured by electrodes attached to the right and left sides of the abdomen when the belt is worn around the waist, and FIG. 21 illustrates a waveform diagram of a heart rate measured by electrodes attached to the right and left parts of the right side of the abdomen when the belt is worn around the waist.

Embodiments of the present invention can be implemented by a computer(s) (including all the devices capable of processing information) through computer readable code on a medium, e.g., a computer-readable recording medium. The medium may include all kinds of recording devices where data readable by a computer system can be stored/transferred. Media may include ROMs, RAMs, CD-ROMs, magnetic tapes, floppy disks, or optical data storages, or the Internet, for example.

Embodiments of the present invention provide an index for quantitatively monitoring progress based on a degree of abdominal fatigue by measuring the degree of abdominal fatigue before and after repeated abdominal muscle exercise. Therefore, electrical stimulation may be applied to the abdomen such that the abdominal muscle exercise does not aggravate the fatigued abdominal muscle. The user may also control the degree of the electrical stimulation.

When a user is performing aerobic exercises such as running, jogging, walking, or stepping, while wearing an abdominal belt including a heart rate measuring sensor at the abdomen and an acceleration measuring sensor at the abdomen and back, the heart rate and acceleration of the user can be measured simultaneously. Accordingly, it is possible to estimate information such as calories expended, thereby enabling quantitative exercise by suggesting an intensity of exercise, for a level of calories expended, for healthy people or patients having difficulty with movement.

Further, a walking pattern of a user can be monitored using the acceleration sensors attached to the front and rear of the belt worn around the waist, and the degree of muscle fatigue can be monitored using an EMG sensor placed around the waist, along the back, for example. In this regard, activity information for patients having difficulty with movement can be monitored, thereby producing information useful for rehabilitative training.

In particular, it is possible to monitor the status of lumbar protection and activity of patients with lumbar troubles and to provide feedback information according to walking patterns of patients, for example, having difficulty with movement, thereby inducing effective rehabilitative training.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A health training/monitoring apparatus, comprising:
an electrical stimulation generator to adjust an electrical stimulation signal based on a degree of fatigue of a muscle of a body, and to generate the adjusted electrical stimulation signal;
a physical activity monitor to monitor a physical activity of a user using at least one of a heart rate measurer and an accelerometer for the body; and
a mode selector selectively driving one of the electrical stimulation generator or the activity output unit of the physical activity monitor based on an output waveform of the accelerometer,
wherein the apparatus is a waist belt or a patch;
wherein the waist belt or the patch comprises:
a first layer comprising a plurality of electrodes for measuring the heart rate, a plurality of electrodes for the electrical stimulation, and a plurality of electrodes for measuring of a electromyographic signal; and
a second layer comprising the accelerometer measuring the acceleration of the physical movement and a predetermined controller;
wherein an airbag layer that is inflatable and deflatable by air is interposed between the first layer and the second layer.

2. The health training/monitoring apparatus of claim 1, wherein the electrical stimulation generator comprises:
an electromyogram detector to detect an electromyographic signal of the body;
a fatigue index calculator to calculate a fatigue index indicating the degree of fatigue by converting the detected electromyographic signal, detected during a predetermined time unit, into a frequency-domain electromyographic signal; and
an electrical stimulation signal generator to adjust the electrical stimulation signal based on the calculated fatigue index and to generate the adjusted electrical stimulation signal.

3. The health training/monitoring apparatus of claim 1, wherein the physical activity monitor comprises:
the heart rate measurer to measure a heart rate using a predetermined electrode attached to the body; and
the accelerometer to measure an acceleration of physical movement of the body; and
wherein the physical activity monitor performs monitoring of physical activity based on at least one of the measured heart rate and the measured acceleration.

4. The health training/monitoring apparatus of claim 3, wherein the accelerometer measures the acceleration of the physical movement in any one of a one-axis direction, two-axis direction, or three-axis direction.

5. The health training/monitoring apparatus of claim 3, wherein the activity output unit further comprises:
a calories expended unit to calculate and output calories expended based on personal information of the user and further based on at least one of the measured heart rate and the measured acceleration.

6. The health training/monitoring apparatus of claim 1, wherein the mode selector selectively drives the physical activity monitor when an output waveform of the accelerometer is greater than a predetermined threshold value or selectively drives the electrical stimulation generator when the output waveform of the accelerometer is not greater than the predetermined threshold value.

* * * * *

UNITED STATES PATENT AND TRADEMARK OFFICE
CERTIFICATE OF CORRECTION

| | |
|---|---|
| PATENT NO. | : 8,620,439 B2 |
| APPLICATION NO. | : 12/379935 |
| DATED | : December 31, 2013 |
| INVENTOR(S) | : Lee et al. |

Page 1 of 1

It is certified that error appears in the above-identified patent and that said Letters Patent is hereby corrected as shown below:

On the Title Page Item [56] (Reference Cited), before "OTHER PUBLICATIONS" insert
-- FOREIGN PATENT DOCUMENTS Republic of Korea Patent Application No. 2002-0094227, filed December 18, 2002
WIPO Patent Application No. 2004/037344, filed May 06, 2004 --.

On the Title Page Item [56] (References Cited - OTHER PUBLICATIONS), insert -- Su-Yong Hong et al., "The Study of Muscle Fatigue Index Searching in terms of Median Frequency Analysis of EMG signals during Isotonic Exercise" Sooyong Hong et al., Medical and Engineering Journal, vol. 24, No. 3, pages 175-188, 2003. --.

On the Title Page Item [56] (References Cited - OTHER PUBLICATIONS), insert -- Korean Office Action Issued for corresponding Korean Application 10-2004-0042507 and English translation issued February 15, 2006. --.

Signed and Sealed this
Twenty-second Day of July, 2014

Michelle K. Lee
*Deputy Director of the United States Patent and Trademark Office*